United States Patent [19]

Sättler et al.

[11] 4,451,365

[45] May 29, 1984

[54] COLUMN CLAMPING DEVICE FOR CHROMATOGRAPHY

[75] Inventors: Günther Sättler, Reinheim; Werner Gunkel, Rossdorf; Manfred Witzgall; Reinhard Look, both of Darmstadt, all of Fed. Rep. of Germany

[73] Assignee: Merck Patent Gesellschaft mit beschrankter Haftung, Fed. Rep. of Germany

[21] Appl. No.: 437,667

[22] Filed: Oct. 29, 1982

[30] Foreign Application Priority Data

Oct. 30, 1981 [DE] Fed. Rep. of Germany ....... 3143075

[51] Int. Cl.³ .............................................. B01D 15/08
[52] U.S. Cl. .................................... 210/198.2; 55/386
[58] Field of Search ......................... 210/198.2; 55/386

[56] References Cited

U.S. PATENT DOCUMENTS

| | | | |
|---|---|---|---|
| 3,250,395 | 5/1966 | Blume | 210/198.2 |
| 3,841,059 | 10/1974 | McCabe | 55/386 X |
| 3,904,527 | 9/1975 | Wilhelmson | 210/198.2 |
| 4,079,009 | 3/1978 | Seiler et al. | 210/198.2 |
| 4,350,595 | 9/1982 | Gunkel | 210/198.2 |

Primary Examiner—John Adee
Attorney, Agent, or Firm—Millen & White

[57] ABSTRACT

The device is a clamping and sealing apparatus for use with separation columns, i.e., chromatographic columns. Sealing elements having sealing means extending therefrom are provided at each end of a column with at least one being movable in an axial direction and controlled by pressure generating means. The sealing members are shaped corresponding to the ends of the column to fit flush against the column and to provide a seal when actuated by the pressure generating means.

4 Claims, 7 Drawing Figures

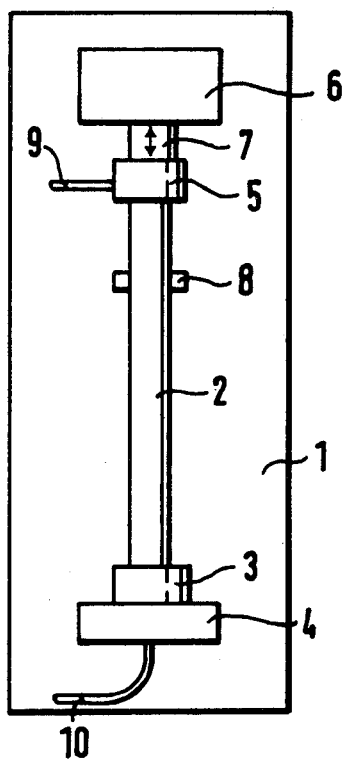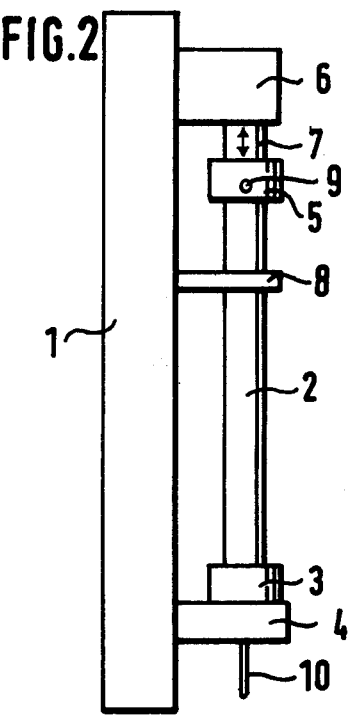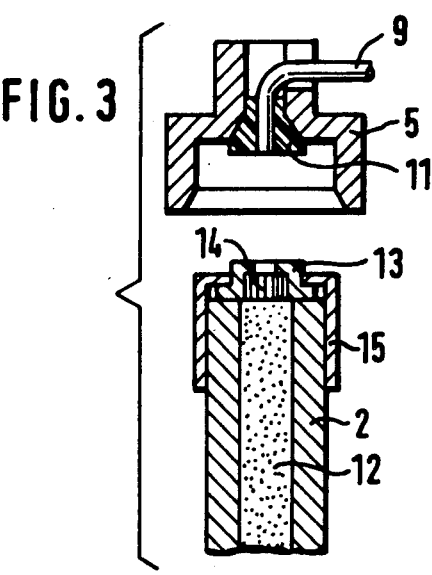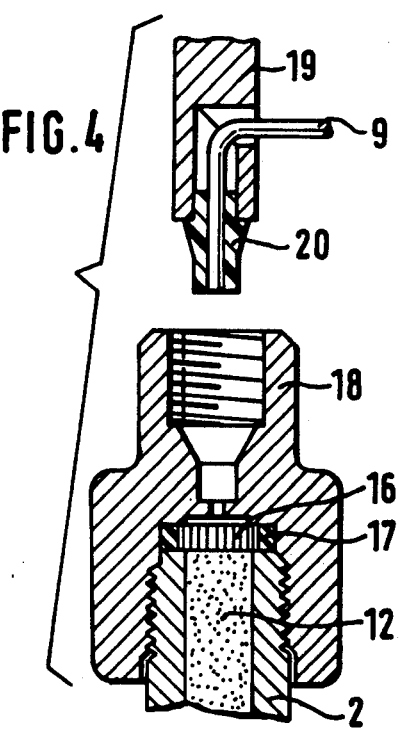

COLUMN CLAMPING DEVICE FOR CHROMATOGRAPHY

BACKGROUND OF THE INVENTION

This invention relates to a device for use in clamping and rapidly changing columns used in liquid chromatography, the device having connectors which are provided with inlets and outlets for the mobile phase passing through the column, and constructed such that the connection between the column and the connector has no dead volume or space resulting from the structural combination of the sealing elements of the column and the connectors.

One important requirement for obtaining good qualitative chromatographic separations is that the connection between the (exchangeable) separating column and the inlets and outlets for the mobile phase, which inlet and outlet are part of the connecting equipment, i.e., fixed thereon, must have no dead volume. Furthermore, this connection should, on the one hand, be easy to engage and disengage so that a column change can be carried out simply and rapidly, and at the same time, should ensure that a full, i.e., hermetic, seal and a lack of dead volume are maintained even after numerous engagements and disengagements of the connection.

In the prior art, attempts to meet these requirements generally involved providing capillary tubes, i.e. small diameter tubes, for the inlet and outlet of the mobile phase and screwing connectors onto the column with pressure screws using coupling means with male ends extending into the tubes and with clamping rings made of metal or plastic. In order to reduce the cross-section of the column to about the cross-section of the capillary tubing, the columns are, as a rule, closed at both ends with reducing threaded joints, which are screwed or clamped onto threaded joints of the connectors.

One variation in this type of device requires that the column be designed as a cartridge closed at both ends with a filter material therein. The filter material is clamped in a tube having reducing threaded joints and connecting threaded joints for the capillary tubes at both ends. The advantage of this design is that, when it is necessary to change the column, only the cartridge containing the adsorbent need be exchanged, whereas the complicated and costly reducing threaded joints can be used repeatedly. Upon changing the cartridge, the capillary tubing must first be removed, at least at one end, before unscrewing the reducing threaded joints.

All of these devices have the disadvantage that connections which are essential to achieve good material, i.e., chromatographic, separation in the column are produced by screwing together manually. There is always the danger during this operation that either an incomplete seal is obtained due to insufficient tightening, or alternatively, the sealing elements are damaged due to over-tightening. Thus, it is impossible for unskilled operators to change a column rapidly and safely. Furthermore, it is also very difficult to automate such a column changing operation.

SUMMARY OF THE INVENTION

Thus, it is an object of the invention to provide a clamping device which permits a rapid column change, which can also be automated if necessary and which ensures an improved reliability in the sealing achieved.

Upon further study of the specification and appended claims, further objects and advantages of this invention will become apparent to those skilled in the art.

This invention relates to a device for clamping and rapidly changing columns for use in liquid chromatography separation, wherein the device has connectors which are provided with inlets and outlets for the mobile phase passing through the column, and wherein the connection between column and connector has no dead volume due to the combined action of the sealing elements of the column and the connectors. The device is characterized by providing an upper and a lower clamping and sealing element having sealing elements compatible with the design of the ends of the column, and wherein at least one of these clamping and sealing elements are movable in the axial direction of the column with the aid of a pressure generating means. Thus, it is possible for the column in the unclamped state to be moved in an axial direction and exchanged, and, in the clamped state, the clamping and sealing elements under a predetermined pressure act in combination with the column to form a seal.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein:

FIG. 1 is a schematic diagram showing a front view of one embodiment of the device according to the invention;

FIG. 2 is a side view of the device of FIG. 1;

FIG. 3 is a partial view in cross-section of one embodiment of a clamping and sealing element combined with a cartridge or column in accordance with the invention;

FIG. 4 is a partial view in cross-section of another embodiment of a clamping and sealing element combined with a column of the type having reducing threaded joints in accordance with the invention;

DETAILED DISCUSSION OF THE INVENTION

Figure 5:
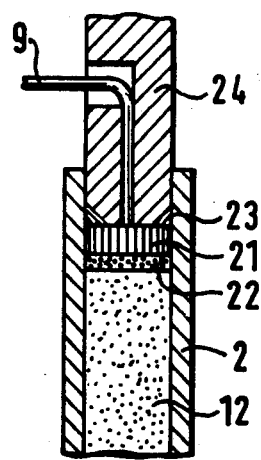
FIG. 5 is a partial view in cross-section of still another embodiment of a clamping and sealing element combined with a column having a compressible packing.

In the drawings, a backing plate 1 is shown with a column 2 held thereon by a lower clamping and sealing element 3. A support 4 is arranged below the lower element 3 and an upper clamping and sealing element 5 is associated with pressure element 6 having a piston 7. A centering piece 8 is located at a position intermediate the upper and lower clamping and sealing elements 3 and 5. A capillary tube 10 for the mobile phase inlet is attached at the bottom, and a capillary for the outlet is attached at the top. A sealing cone 11 is especially designed for connecting a column cartridge 2 having the column packing 12 therein. A sealing ring 13 having a frit 14 inserted therein is fixed on the end of the column cartridge 2 by means of a cap 15 which is stuck or pressed thereon in a conventional manner.

In an alternative embodiment, a frit 16 and a sealing ring 17 are positioned inside a reducing threaded joint 18. A clamping and sealing element 19 especially adapted for columns having reducing threaded joints is employed in cooperation with a correspondingly shaped sealing cone 20.

In still another embodiment a frit 21 and a layer of beads 22 are associated with a seal 23 at the outlet end.

Figure 6:
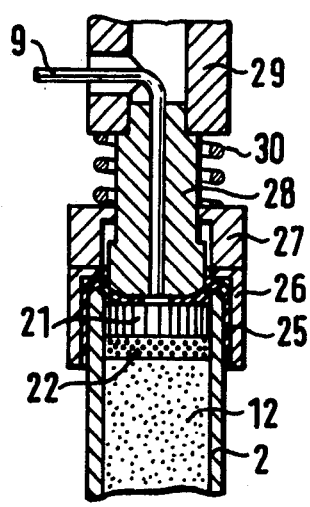
FIG. 6 is a partial view in cross-section of yet still another embodiment of a clamping and sealing element combined with a column having a compressible packing and a diaphragm seal.

In yet still another embodiment of the device the clamping and sealing element 24 is associated with a flexible diaphragm 25 and a clamping cap 26 as shown in FIG. 6. A pressure ring 26 holds the clamping cap 26 fixed on the column 2. Furthermore, a piston 28 is associated with a clamping element 29 and a spring element 30 to achieve a proper seal by having the piston 28 urged downwardly into sealing engagement.

Figure 7:
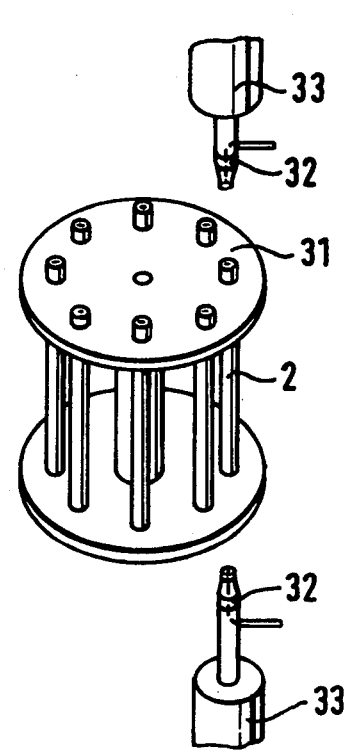
FIG. 7 is a schematic view, in perspective, of one example of the use of the clamping device according to the invention, in combination with an automatic column changing device.

All of these embodiments can be employed with a rotating magazine 31 shown in FIG. 7. Furthermore, to achieve clamping and sealing in this device, a clamping and sealing element 32 is provided at each end of the column 2 associated with a pneumatic cylinder 33 which provides a constant force of clamping and sealing for each respective change of columns 2.

As is already evident from the examples represented in the drawings, the device according to the invention can be used in combination with all possible designs of column. In order to be compatible with various designs of column it is only required that the sealing part of the clamping and sealing element, i.e., 5, 19, 20, 24, 27 and 28 be shaped to suit the particular column employed. The principle according to the invention, i.e., that the column 2 is clamped between two clamping and sealing elements without screwing, is unaffected by the particular type of column employed. Thus, the invention can be employed with columns having reducing threaded joints corresponding to FIG. 4, which are still mainly in use today, cartridge columns corresponding to FIG. 3, and even with special columns, i.e., those for preparative use, with compression of the packing, corresponding to the embodiment of FIGS. 5 and 6. The clamping and sealing elements 3, 5, 19, 24, 27 and 28 can be made of any material that withstands the applied pressure like metal or a plastic material. The sealing cones 11 and 20, however, are preferably made of a plastic material that is able to provide for the necessary sealing. An especially preferred material is PTFE or a similar material.

The clamping and sealing devices are preferably formed to fit flush when being in engagement with the conjugate part of the column 2. Since, however, the sealing is provided mainly by the part of the sealing cones 11 and 20 facing the column 2, tolerances are possible without adverse effect.

The column is always clamped in axial direction with a constant force which is predetermined by the clamping device used and thus is independent of the user. For this purpose, as discussed previously, a pressure element 6 is provided which presses the clamping and sealing element 5 onto the column 2 by means of the piston 7 and with the necessary opposing pressure being produced by the fixed lower support 4 and the lower clamping and sealing element 3. The piston 7 can, in one form, also be an integral part of the clamping and sealing element 5. A typical pressure element 6 can be, for example, a spring element with the spring being tensioned by pressure generated by a lever, for example, a toggle-action tensioner. Alternatively, the necessary clamping force can also be generated by means of a pressure screw acting on the spring element. All of these predetermined pressure generating devices are conventional and well known to those skilled in the art.

Although various pressure elements 6 have been described, it is preferred that a pneumatic cylinder is employed as the pressure element 6, which cylinder can be supplied by a compressed air line in the laboratory, or by an external cylinder of compressed gas.

The working stroke provided for removing and replacing the column 2, i.e., the distance which the upper clamping and sealing element 5 travels on clamping or unclamping the column is preferably about 10 to 20 mm, so that, in the unclamped state, the column is freely accessible providing sufficient clearance to be easily exchanged. In order to adjust the free space between the upper 5 and lower clamping and sealing elements 3 to different lengths of column, it should be possible to adjust the height of the lower support 4. For this purpose, either a device for continuous height adjustment can be provided, or various locking steps can be provided for columns of different standard lengths. All these devices are conventional to a skilled worker.

The insertion of a new column is carried out in such a way that, if appropriate, after adjusting the height of the lower support 4 to the length of the column, the column is inserted into the lower clamping and sealing element 3 and, after aligning the column 2 with the aid of the centering piece 8 (for example, in the form of a V-shaped recess), the pressure element 6 is actuated, by which means the upper clamping and sealing element 5 is pressed onto the column 2. Thus, exchanging a column takes only a few seconds and can also be carried out by an unpracticed operator without any difficulty. It is ensured that, due to the constant predetermined applied pressure provided by the pneumatic cylinder or the spring tension, that the column is in fact reliably sealed, but that the sealing elements are not overstressed by excessive pressure generation.

Exchange of the columns can also be completely automated by using the device according to the invention. More specifically, several columns 2 can be mounted on a rotating magazine 31 as shown in FIG. 7. The clamping device according to the invention in this case has two pressure elements in the form of pneumatic cylinders 33 at each end which move the clamping and sealing elements 32. Thus, by actuating the pneumatic cylinders 33, the column 2 is released at both ends and can be replaced by any other desired column by rotating the holder 31. Clearly, various different types of columns can also be used in this device after appropriate adjustment of the clamping and sealing elements 32. Alternatively, other devices for column changing can be employed instead of a rotating magazine as will be obvious to those skilled in the art.

The term "column" in the present application is to be understood in a broad sense. Thus, it refers not only to the actual separating columns, but also, for example, to pre-separation columns, enrichment columns, or, for example, also to sample tubes which contain a sample to be separated.

The automation made possible by the clamping device according to the invention allows, for example, separations of different samples of substance, which are present in sample tubes or adsorbed in enrichment columns in a device for changing columns according to FIG. 7, to be run on one separating column, or, when also employing a changing device for the separating column, on different columns, automatically and in a pre-programmed manner, for example, overnight. The invention makes available a valuable new device with which the range of uses of liquid chromatographic separating processes can be further enhanced.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a device for rapidly changing columns of the type generally used in liquid phase chromatography, said device comprising connectors for each end of a column with respective inlet and outlet for passage into and out of the column of the mobile phase, and the connectors being adapted so that there is no dead volume between column and connector, when connected thereon, due to the combined action of sealing means employed therewith, the improvement wherein said connectors comprise:

upper and lower clamping and sealing elements (3 and 5) having sealing members (11, 20, 23 and 28) extending therefrom and said sealing member shaped to be compatible with the ends of the column to which they are to be sealed against at the inlet and outlets of the column, with said sealing elements having means for passing the liquid phase therethrough, and at least one of said upper and lower clamping and sealing elements (3 and 5) being movable in the axial direction of the column for clamping and unclamping the column; and pressure means for moving at least one of said upper and lower clamping and sealing elements (3 and 5) selectively between an unclamped position and a clamped position at which said pressure means is adapted for exerting a predetermined pressure on the column (2) to ensure substantially complete sealing, and wherein said pressure means comprises a pneumatic cylinder associated with means for moving said at least one of the upper clamping and sealing elements.

2. A device according to claim 1, wherein said pneumatic cylinder is fed compressed gas from an external source.

3. A device according to claim 1 further comprising a rotating magazine having a plurality of columns loaded thereon, and said upper and lower clamping elements being both movable in the axial direction and having respective pressure means associated therewith.

4. A method of use of the device of claim 3 comprising changing columns by unclamping a first column on said rotating magazine, rotating said magazine to position another column for clamping with said clamping and sealing elements, and clamping and sealing said other column.

* * * * *